(12) United States Patent
Willey et al.

(10) Patent No.: US 11,369,682 B2
(45) Date of Patent: Jun. 28, 2022

(54) LIGHT ACTIVATED GASOTRANSMITTER GENERATING COMPOSITIONS

(71) Applicant: Noxsano Inc., Columbus, OH (US)

(72) Inventors: Alan Willey, Columbus, OH (US); Stevan Samuel, Cincinnati, OH (US)

(73) Assignee: Noxsano Inc., Columbus, OH (US)

( * ) Notice: Subject to any disclaimer, the term of this patent is extended or adjusted under 35 U.S.C. 154(b) by 0 days.

(21) Appl. No.: 16/392,995

(22) Filed: Apr. 24, 2019

(65) Prior Publication Data

US 2019/0328878 A1 Oct. 31, 2019

Related U.S. Application Data

(60) Provisional application No. 62/662,573, filed on Apr. 25, 2018.

(51) Int. Cl.
| | | |
|---|---|---|
| *A61K 41/00* | (2020.01) | |
| *A61P 17/10* | (2006.01) | |
| *A61P 17/02* | (2006.01) | |
| *A61K 9/06* | (2006.01) | |
| *A61N 5/06* | (2006.01) | |
| *A01N 59/00* | (2006.01) | |
| *A01N 25/00* | (2006.01) | |

(52) U.S. Cl.
CPC .......... *A61K 41/0057* (2013.01); *A01N 25/00* (2013.01); *A01N 59/00* (2013.01); *A61K 9/06* (2013.01); *A61N 5/062* (2013.01); *A61N 5/0616* (2013.01); *A61P 17/02* (2018.01); *A61P 17/10* (2018.01); *A61L 2300/114* (2013.01)

(58) Field of Classification Search
None
See application file for complete search history.

(56) References Cited

U.S. PATENT DOCUMENTS

| | | |
|---|---|---|
| 6,225,273 B1 | 5/2001 | Willey et al. |
| 8,222,242 B2 | 7/2012 | Boss et al. |
| 8,440,849 B2 | 5/2013 | Conoci et al. |
| 8,685,466 B2 | 4/2014 | Piergallini et al. |
| 2012/0181163 A1 | 7/2012 | Inagaki et al. |
| 2015/0024052 A1 | 1/2015 | Doxey |
| 2015/0210964 A1* | 7/2015 | Willey ............... C11D 11/007 424/665 |
| 2017/0064964 A1 | 3/2017 | Bell et al. |
| 2018/0116920 A1* | 5/2018 | Hemmrich ............ A61Q 19/00 |
| 2018/0221210 A1 | 8/2018 | Willey et al. |

FOREIGN PATENT DOCUMENTS

| | | |
|---|---|---|
| EP | 3097169 A1 | 11/2016 |
| WO | 2018147986 A1 | 8/2018 |

OTHER PUBLICATIONS

International Search Report; ISA/US Commissioner for Patents; International Application No. PCT/US2019/028856; dated Jul. 30, 2019; 2 pages.
Written Opinion of the International Searching Authority; ISA/US Commissioner for Patents; International Application No. PCT/US2019/028856; dated Jul. 30, 2019; 6 pages.
International Preliminary Report on Patentability; ISA/US Commissioner for Patents; International Application No. PCT/US2019/028856; dated Oct. 27, 2019; 7 pages.
First Examination Report; Intellectual Property India; Indian Application No. 202027051333; dated Oct. 28, 2021; 5 pages.
Chinese Office Action; The State Intellectual Property Office of People's Republic of China; Chinese Application No. 201980042939.5; dated Aug. 27, 2021; 7 pages.
Extended European Search Report; European Patent Office; European Application No. 19792673.6; dated Mar. 1, 2022; 8 pages.

* cited by examiner

*Primary Examiner* — H. Sarah Park

(74) *Attorney, Agent, or Firm* — Taft Stettinius & Hollister LLP

(57) ABSTRACT

A composition comprising an organic photoactivator, a gasotransmitter salt which converts into a gasotransmitter via electron transfer, and an electron donor which donates an electron to the photoactivator when the photoactivator is in a photo-excited state.

20 Claims, 1 Drawing Sheet

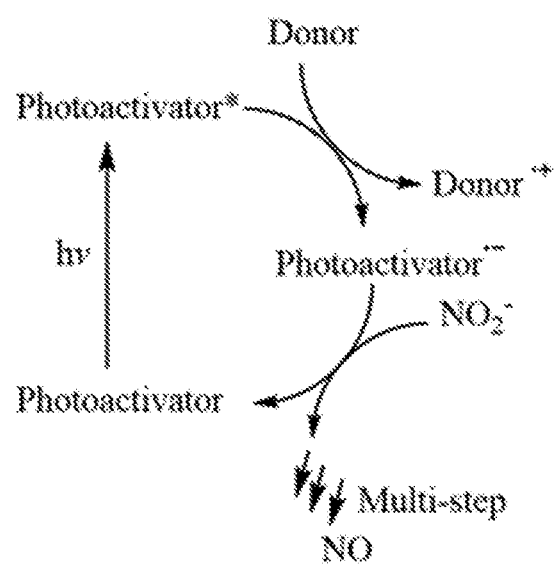

LIGHT ACTIVATED GASOTRANSMITTER GENERATING COMPOSITIONS

CROSS REFERENCE TO RELATED APPLICATIONS

This application claims priority to U.S. Provisional Patent Application Ser. No. 62/662,573 filed on Apr. 25, 2018, which is incorporated by reference herein in its entirety.

FIELD

The present disclosure provides compositions that include one or more photoactivators to generate one or more gasotransmitters, including, without limitation, nitric oxide and hydrogen sulfide, as well as to therapeutic methods applying same, and to dressing articles and systems for the application thereof to target tissue sites, as well as methods to generate one or more gasotransmitters at a site amenable to application of the compositions through the application of light, such as medicaments, including, without limitation, ointments, salves, creams, and the like.

BACKGROUND

In the last two decades the importance of gasotransmitters in biological processes has been recognized, especially that of nitric oxide (NO) which has been implicated in a number of bioregulatory processes including normal physiological control of blood pressure, macrophage destruction of foreign pathogens, and neurotransmission. Recent research has further demonstrated that nitric oxide possesses a broad-spectrum of antimicrobial activity and may be used as an alternative to conventional antibiotics for drug resistant bacteria. In addition, nitric oxide may also be used to alleviate inflammation and promote wound healing.

However, nitric oxide is a gas at ambient temperature and atmospheric pressure, and it has a short half-life in physiological milieu. Thus, it is relatively challenging to deliver nitric oxide in a controlled and targeted manner and use nitric oxide to treat bacterial infection and/or diseases. The application of nitric oxide has been relatively limited because of the absence of a controlled and targeted delivery method or material.

Therefore, there is a need for a gasotransmitter delivery system, especially for nitric oxide, that can deliver these species in a controlled and targeted manner.

SUMMARY

An aspect of the present disclosure provides a composition comprising an organic photoactivator; a gasotransmitter salt which converts into a gasotransmitter via electron transfer; and an electron donor which donates an electron to the photoactivator when the photoactivator is in a photo-excited state. In some embodiments, the photoactivator is selected from benzophenone, anthraquinone, thioxanthone, and ketocoumarin, and derivatives thereof. In some embodiments, the photoactivator is water soluble.

In some embodiments, the electron donor is selected from alcohols, amines, thiols, sugars, and boranes, and derivatives thereof. In some embodiments, the electron donor is selected from secondary alcohols, tertiary amines, and heteroaromatic thiols, and derivatives thereof. In some embodiments, the electron donor is selected from isopropyl alcohol, 2-hexanol, cyclohexanol, triethylamine, ethylene diamine tetracarboxylic acid, diethylene triamine pentacarboxylic acid, and diethylene triamine pentaphosphonic acid.

In some embodiments, the gasotransmitter salt is a nitrite or nitrate salt with the formula:

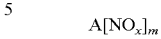

wherein x is 2 or 3; wherein A is selected from monovalent cations, divalent cations, and trivalent cations; wherein m is 1, 2 or 3. In some embodiments, A is selected from aluminum, barium, calcium, cobalt, chromium, copper, iron, lithium, potassium, rubidium, magnesium, manganese, molybdenum, nickel, sodium, titanium, vanadium, zinc, ammonium, alkyl-ammonium, and aryl-ammonium, and mixtures thereof.

In some embodiments, the gasotransmitter salt is a sulfate, sulfite, or thiosulfate salt with the formula:

wherein A is selected from monovalent cations, divalent cations, and trivalent cations; wherein a is 1 or 2, b is 3 or 4, and y is 1, 2 or 3. In some embodiments, A is selected from aluminum, barium, calcium, cobalt, chromium, copper, iron, lithium, potassium, rubidium, magnesium, manganese, molybdenum, nickel, sodium, titanium, vanadium, zinc, ammonium, alkyl-ammonium, and aryl-ammonium, and mixtures thereof.

In some embodiments, the composition is dissolved in water to form an aqueous solution comprising an electron donor which donates an electron to the photoactivator when the photoactivator is in a photo-excited state and/or oxidized state. In some embodiments, the photoactivator is activated to the photo-excited state by excitation with incident radiation of a wavelength between about 300 nm and about 750 nm.

In some embodiments, the photo-excited state lifetime is greater than about 50 nanoseconds. In some embodiments, the photo-excited state of the photoactivator has an energy greater than about 100 kJ/mol more than a ground state of the photoactivator.

In some embodiments, the photoactivator includes a photoactive moiety selected from benzophenone and thioxanthone and derivatives thereof. In some embodiments, the photoactivator comprises a hydrophilic moiety selected from the group consisting of alcohol, amine, amide, carboxylic acid, sulfonic acid and phosphatealkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, 2-ethyl-2-oxazoline, hydroxyethyl methacrylate, vinyl pyridine-N-oxide, diallyl dimethyl ammonium chloride, maleic acid, lysine, isopropyl acrylamide, styrene sulfonic acid, vinyl methyl ether, vinyl phosphonic acid, ethylene imine, and mixtures thereof.

In some embodiments, the composition further comprises a hydrophobic base and an amphiphilic compound. In some embodiments, the hydrophobic base comprises a material selected from the group consisting of natural fats, synthetic fats, waxes, and oils.

In some embodiments, the composition is in a form selected from the group consisting of ointments, salves, and creams.

In some embodiments, the composition further comprises a moisture activated active pharmaceutical ingredient.

In some embodiments, the photoactivator is activated to the photo-excited state by excitation with incident radiation of a wavelength between about 320 nm and about 420 nm.

In some embodiments, the gasotransmitter salt is sodium nitrite or sodium sulfite.

Another aspect of the present disclosure provides a method of making a benefit active. In some embodiments, the method comprises exposing a composition of the present disclosure to light. In some embodiments, the benefit active is used for wound healing. In some embodiments, the benefit active is used as an antimicrobial. In some embodiments, the benefit active is used as an anti-biofilm. In some embodiments, the benefit active is used for bleaching. In some embodiments, the benefit active is used for disinfection. As will be understood by one of ordinary skill in the art, many other uses for the benefit active of the present disclosure are contemplated to be within the scope of the present disclosure.

Another aspect of the present disclosure provides a method of treating acne vulgaris. In some embodiments, the method comprises contacting the surface of skin affected by acne vulgaris with a composition of the present disclosure; and exposing the composition to light.

Another aspect of the present disclosure provides a method of treating a wound. In some embodiments, the method comprises contacting the surface of wounded tissue with a composition of the present disclosure; and exposing the composition to light.

Another aspect of the present disclosure provides a method of treating skin. In some embodiments, the method comprises contacting a skin surface with a composition of the present disclosure; and exposing the composition to light.

Another aspect of the present disclosure provides a method of disinfecting a surface. In some embodiments, the method comprises contacting the surface with a composition of the present disclosure; and exposing the composition to light.

Another aspect of the present disclosure provides a method of removing biofilm from a surface. In some embodiments, the method comprises contacting a biofilm with a composition of the present disclosure; and exposing the composition to light.

BRIEF DESCRIPTION OF THE DRAWINGS

The above-mentioned aspects of embodiments will become more apparent and will be better understood by reference to the following description of embodiments taken in conjunction with the accompanying drawing, wherein:

FIG. 1 is a schematic showing a general representation of the photoactivation of a photoactivator resulting in the donation of an electron by an electron donor followed by conversion of a nitrite salt to nitric oxide, in accordance with an embodiment of the present invention.

DETAILED DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Some embodiments of the present disclosure are related to some embodiments described in U.S. patent application Ser. No. 15/874,665, filed Jan. 18, 2018, which is incorporated herein by reference in its entirety.

In some embodiments, the present disclosure provides compositions that include water soluble photoactivators, an electron donor, and a soluble gasotransmitter salt. In some embodiments, the present disclosure also provides photocatalyzable compositions comprising a photoactivator, an electron donor, and a gasotransmitter salt. In some embodiments, the present disclosure also provides methods for providing one or more health benefits to a subject by exposing a targeted site to the gasotransmitter generating composition. In some embodiments, the present disclosure provides methods for cleaning and disinfecting surfaces. In some embodiments, the amount and rate of the release of gasotransmitter is regulated by adjusting the formulation and/or the current or photon flux.

Photoactivator

In some embodiments, the water soluble photoactivators of the present disclosure may comprise a photoactive moiety and a water solubilizing moiety. Without wishing to be bound by any particular theory, it is believed that the incorporation of polar functional groups, such as alcohol, amine, amide, carboxylic acid, sulfonic acid and phosphate groups, which either ionize or are capable of relatively strong intermolecular forces of attraction with water (hydrogen bonding), will usually result in analogues with an increased water solubility. In some embodiments, acidic and basic groups are useful. In some embodiments of the present disclosure, the term "water solubilizing moiety" refers to a moiety that is attracted to water and dissolves in water to form a homogenous solution. In some embodiments, the water solubilizing moiety is selected from the group consisting of alcohol, amine, amide, carboxylic acid, sulfonic acid and phosphate groups. In another embodiment, the hydrophilic moiety is selected from the group consisting of water soluble oligomers, water soluble polymers, and water soluble copolymers. In some embodiments, the hydrophilic moiety may be selected from carboxylic acid and sulfonic acid. In some embodiments, the hydrophilic group is selected from the group consisting of alkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, 2-ethyl-2-oxazoline, hydroxyethyl methacrylate, vinyl pyridine-N-oxide, diallyl dimethyl ammonium chloride, maleic acid, lysine, arginine, histidine, aspartic acid, glutamic acid, serine, threonine, asparagine, glutamine, isopropyl acrylamide, styrene sulfonic acid, vinyl methyl ether, vinyl phosphonic acid, ethylene imine, and mixtures thereof. In some embodiments, the hydrophilic moiety may be selected from the group consisting of alkylene oxide oligomer polymers, alkylene oxide oligomer copolymers, vinyl alcohol, vinyl pyrrolidone, acrylic acid, acrylamide, cellulose, and mixtures thereof. In some embodiments of the present disclosure, the term "photoactive moiety" refers to an organic conjugated moiety that is capable of absorbing a photon of light and thereby forming an excited state (singlet or triplet). One of ordinary skill in the art would appreciate that the term "photoactive moiety" does not, however, refer to a charge-transfer excited state. One of ordinary skill in the art would also understand that the photoactive moieties, as disclosed herein, may include a single moiety or a combination of two, three, four or any other number of moieties known in the art.

In some embodiments of the present disclosure, the photoactive moiety is selected from the group consisting of xanthones, xanthenes, thioxanthones, thioxanthenes, phenothiazines, fluoresceins, benzophenone, quinones, anthraquinones, ketocoumarins, alloxazines, isoalloxazine, flavins, derivatives thereof, and mixtures thereof. In some embodiments, the photoactive moiety is a water-soluble derivative of benzophenone. In some embodiments, the photoactive moiety is benzophenone tetracarboxylic acid.

It is still further another aspect of the present disclosure that the photoactive moiety absorbs light between about 300 nm and about 750 nm, about 320 nm and about 600 nm, about 350 nm and about 420 nm, and about 350 nm and about 400 nm to form a reducing excited state.

In some embodiments of the present disclosure, the photoactivator can be activated to a photo-excited state by excitation with incident radiation of a wavelength greater than 350 nm. In some embodiments, the photoactivator can be activated to a photo-excited state by excitation with incident radiation of a wavelength between about 350 nm and about 420 nm. In some embodiments, the photo-excited state lifetime is greater than about 0.5 nanoseconds, 1 nanosecond, 10 nanoseconds, 50 nanoseconds, 100 nanoseconds, 300 nanoseconds, and 500 nanoseconds. In some embodiments, the photo-excited state of the photoactivator has an energy greater than about 100 kJ/mol, 150 kJ/mol, 200 kJ/mol, and 300 kJ/mol more than a ground state of the photoactivator.

In some embodiments, the photoactivator can be excited to a "singlet state," as such term is known in the art. In some embodiments, the photoactivator can be excited to a "triplet state," as such term is known in the art.

Photocatalyzable Composition

In some embodiments, the present disclosure also provides a photocatalyzable composition that includes the photoactivator, an electron donor, and a gasotransmitter salt.

In some embodiments, the photocatalyzable composition may be an aqueous solution, a solid, a gel, or incorporated into a material, such as a film. In another embodiment, the individual components of the photocatalyzable composition may be incorporated into both an aqueous solution and a material, such as a film. In another embodiment, the photoactivator may be included in a film or gel and the electron donor and/or gasotransmitter salt may be included in an aqueous solution or gel. In another embodiment, the photoactivator may be included in a hydrogel. It will be understood by one of ordinary skill in the art that, in this particular embodiment, a film comprising a photoactivator may be applied to the surface and an aqueous solution or gel comprising an electron donor and gasotransmitter salt may be applied separately. It will be further understood by one of ordinary skill in the art that if the applied photocatalyzable composition according to an embodiment takes the form of a film, the film must transmit the wavelengths of light required for the formation of the excited state of the photoactivator.

It will be appreciated by one of ordinary skill in the art that, in some embodiments, the relative concentration of the photoactivator, electron donor, and gasotransmitter salt may be determined for any given photocatalyzable composition depending upon the desired gasotransmitter production and duration of that production considering the amount and wavelength of light to which the photocatalyzable composition is to be exposed over time.

In the case of an aqueous composition according to some embodiments, the composition may comprise from 1% to 99%, by weight of the composition, of water. It will therefore be understood by one of ordinary skill in the art that the photocatalyst can be in concentrated or diluted form, and it will be appreciated by one of ordinary skill in the art that the relative concentration of the photocatalyst may be determined in accordance with the desired gasotransmitter production and duration of that production. It is contemplated that, in some embodiments, all or a portion of the water may be replaced with another solvent such as ethanol, glycol, glycol-ethers, glycerin, water soluble acetates, and alcohols. It is also contemplated that the aqueous composition in accordance with some embodiments may be formed into a hydrogel to facilitate delivery to the site of action. Hydrogel forming polymers suitable for some embodiments of the present disclosure include but are not limited to crosslinked poly(acrylic acid), crosslinked poly(vinylpyrrolidone), and crosslinked polyethylene glycol.

As noted above, some embodiments of the present disclosure provide photocatalyzable compositions that include the photoactivator, an electron donor, and gasotransmitter salt. In such embodiments it will be understood that the photocatalyst can be excited into a singlet and/or triplet state via activation by light. It will also be understood that the gasotransmitter salt can be converted into a gasotransmitter such as nitric oxide upon reaction with the photocatalyst in an activated singlet and/or triplet state after exposure to light. It will be understood that the photocatalyst is unreactive with the gasotransmitter salt without activation by light.

The photocatalyzable composition in accordance with some embodiments of the present disclosure is a system responsive to light, including, without limitation, visible, ultraviolet, and/or infrared light. In some embodiments, the system is responsive to ultraviolet and visible light. In some embodiments, photon transfer from the light source to the photocatalyst allows the reaction to progress to create a gasotransmitter. In some embodiments, the nitric oxide may act to control blood pressure, macrophage destruction of foreign pathogens, and neurotransmission. In some embodiments, the nitric oxide may provide a broad-spectrum of antimicrobial activity, alleviate inflammation, and promote wound healing.

Electron Donor

The photocatalyzable composition in accordance with some embodiments of the present disclosure comprises an electron donor. It will be understood to those skilled in the art that photocatalytic reduction and oxidation chemistries differ from conventional, energy-transfer photochemistry in that the photocatalytically-induced transfer of electrons can result in chemical transformation of reagents and reduction or oxidation of the gasotransmitter salt to produce a gasotransmitter capable of providing a beneficial result.

As used herein, the term "electron donor" means "a compound or moiety which donates an electron to the photoactivator when the photoactivator is in a photo-excited or oxidized state. This electron transfer process is normally a rapid and reversible process.

The ability of an electron donor to donate an electron to the excited photoactivator is generally described in Turro, N.J., V. Ramamurthy, and J. C. Scaiano, *Principles of Molecular Photochemistry: An Introduction*, Chapter 7, p. 41 (University Science Books 2009, Paperback edition). It is understood that the reaction between the reactants is favored when the Gibbs free energy (delta G) is less than 0.

It will further be understood to those skilled in the art that any electron transfer between species comprising a photocatalyzable composition in accordance with some embodiments of the present disclosure further requires effective Brownian collision to occur between the reacting species. Additionally, effective electron transfer between the photochemically excited state of the photoactivator and any species comprising the photocatalyzable composition (e.g. the electron donor) may further depend on the lifetime of the excited state of the photoactivator, the concentration of the photoactivator, and the concentration of the electron donor.

The electron donor in accordance with some embodiments of the present disclosure may be any species that donates an electron to the photoactivator when the photoactivator is in a photo-excited state and/or oxidized state. In some embodiments, this electron transfer process is a rapid and reversible process.

In some embodiments, a suitable electron donor can be selected from the group consisting of alcohols, amines, thiols, sugars, and boranes, and derivatives thereof. In some embodiments, the electron donor is selected from secondary alcohols, tertiary amines, and heteroaromatic thiols, and derivatives thereof. In some embodiments, the electron donor is selected from isopropyl alcohol, 2-hexanol, cyclohexanol, triethylamine, ethylene diamine tetracarboxylic acid, diethylene triamine pentacarboxylic acid, and diethylene triamine pentaphosphonic acid.

In some embodiments, the photocatalyzable composition is an aqueous composition, and the electron donor is a water soluble species selected from one or more of the groups disclosed herein.

Referring to FIG. 1 and without wishing to be bound to any particular theory, it is believed that light absorbed by the photoactivator converts the photoactivator to an excited state (singlet, triplet, etc.). It is also believed that the excited state is quenched by the donor, which transfers an electron from the donor to the photoactivator. It is further believed that the formed one electron reduced state of the photoactivator (PA$^-$.) initiates the process to reduce nitrite to nitric oxide and returns the photoactivator to ground state.

Gasotransmitter Salt

In some embodiments, the electrochemical composition of the present disclosure comprises a gasotransmitter salt. When used in the electrochemical composition in accordance with some embodiments of the present disclosure, the gasotransmitter salt is converted into a gasotransmitter by reduction.

In one aspect of the present disclosure, the gasotransmitter salt is a nitrite or nitrate salt with the formula:

$$A[NO_x]_m$$

wherein x is 2 or 3; A is selected from the group consisting of monovalent cations, divalent cations, and trivalent cations; wherein m is 1, 2 or 3. In some embodiments, A is selected from the group consisting of aluminum, barium, calcium, cobalt, chromium, copper, iron, lithium, potassium, rubidium, magnesium, manganese, molybdenum, nickel, sodium, titanium, vanadium, zinc, ammonium, alkyl-ammonium, aryl-ammonium, and mixtures thereof. In some embodiments, A is selected from the group consisting of lithium, sodium, potassium, magnesium, calcium, ammonium, and mixtures thereof.

In another aspect of the present disclosure, the gasotransmitter salt is a sulfate, sulfite, or thiosulfate salt with the formula:

$$A[S_aO_b]_y$$

wherein A is selected from the group consisting of monovalent cations, divalent cations, and trivalent cations. In some embodiments, A is selected from the group consisting of aluminum, barium, calcium, cobalt, chromium, copper, iron, lithium, potassium, rubidium, magnesium, manganese, molybdenum, nickel, sodium, titanium, vanadium, zinc, ammonium, alkyl-ammonium, aryl-ammonium, and mixtures thereof. In some embodiments, A is selected from the group consisting of lithium, sodium, potassium, magnesium, calcium, ammonium, and mixtures thereof. In some embodiments, a is 1 or 2, b is 3 or 4, and y is 1, 2 or 3.

Optional Additives

The photocatalyzable compositions in accordance with some embodiments of the present disclosure may also contain additional adjunct additives. The precise nature of these additional components and levels of incorporation thereof will depend on the physical form of the composition, and the precise nature of the cleaning, disinfecting, or health benefit for which it is to be used. It will be understood that some of the adjunct additives noted herein may have photoactive and/or electron donor properties, but it will be further understood that such additives will not replace the components noted herein. It also will be understood that optional additives typically will not be of such a character or be present in such amounts as would functionally defeat the photoactivation of the photoactivator component.

Topical Compositions

Some embodiments of the present disclosure also provide topical compositions. One of ordinary skill in the art understands that the topical composition in accordance with some embodiments will be substantially transparent to the wavelength of light absorbed by the photoactivator to permit the functionally effective photoactivation thereof. In some embodiments, the degree of transparency needed to ensure that the composition generates the desired gasotransmitter will depend on the application. In some embodiments, sufficient light must penetrate the composition of the present disclosure to yield a beneficial flux of the gasotransmitter. In some embodiments, a topical composition of the present disclosure may be in the form of a hydrogel. "Hydrogel," as used herein, refers to a hydrophilic gel comprising a gel matrix and water. In some embodiments, a topical composition of the present disclosure comprises at least one polyhydric alcohol, at least one viscosity increasing agent, and water.

Polyhydric alcohols that may be present in a composition of the present disclosure in accordance with some embodiments include, but are not limited to, glycerol, propylene glycol, polyethylene glycol, polypropylene glycol, triethylene glycol, neopentyl glycols, triethanolamine, diethanolamine, ethanolamine, butylene glycol, polyethylene glycol, n-methyl diethanolamine, isopropanolamine, sorbitol, arabitol, erythritol, HSH, isomalt, lactitol maltitol, mannitol, xylitol, threitol, ribitol, galactitol, fucitol, iditol, inositol, volemitol, and any combination thereof. In some embodiments, a composition of the present disclosure comprises glycerol.

A polyhydric alcohol may be present in a composition of the present disclosure in accordance with some embodiments in an amount of about 1% to about 30% by weight of the composition or any range and/or individual value therein, such as, but not limited to, about 1% to about 20% or about 5% to about 15% by weight of the composition. In some embodiments, a polyhydric alcohol is present in a composition of the present disclosure in an amount of about 1%, 2%, 3%, 4%, 5%, 6%, 7%, 8%, 9%, 10%, 11%, 12%, 13%, 14%, 15%, 16%, 17%, 18%, 19%, or 20% by weight of the composition of the present disclosure or any range and/or individual value therein.

Viscosity increasing agents that may be present in a composition of the present disclosure in accordance with some embodiments include, but are not limited to, a carboxypolymethylene; a polyacrylic polymer such as polyacrylic acid, a polyacrylate polymer, a cross-linked polyacrylate polymer, a cross-linked polyacrylic acid, and mixtures thereof a cellulose ether such as hydroxyalkyl cellulose polymers such as hydroxypropyl methyl cellulose (HPMC), hydroxypropyl cellulose, hydroxyethyl cellulose, methyl cellulose, carboxymethyl cellulose, and mixtures thereof a methacrylate; a polyvinylpyrrolidone; cross-linked polyvinyl pyrrolidone; polyvinylpyrrolidone-vinyl acetate copolymer; polyvinyl alcohol; polyethylene oxide; polyethylene glycol; polyvinyl alkyl ether-maleic acid copolymer; a carboxy vinyl polymer; a polysaccharide; a gum such as sodium alginate, carrageenan, xanthan gum, gum acacia, arabic gum, guar gum, pullulan, agar, chitin, chitosan, pectin, karaya gum, zein, hordein, gliadin, locust bean gum, *Tragacantha*, and mixtures thereof; a protein such as collagen, whey protein isolate, casein, milk protein, soy protein, gelatin, and mixtures thereof; a starch such as maltodextrin, amylose, high amylose starch, corn starch, potato starch, rice starch, tapioca starch, pea starch, sweet potato starch, barley starch, wheat starch, waxy corn starch, modified starch (e.g. hydroxypropylated high amylose starch), dextrin, levan, elsinan, gluten, and mixtures thereof; bentonite; calcium stearate; ceratonia; colloidal silicon dioxide; dextrin; hypromellose; polycarbophil; kaolin; saponite; sorbitan esters; sucrose; sesame oil; tragacanth; potassium alginate; povidone; sodium starch glycolate; phospholipids; and any combination thereof.

In some embodiments, a composition of the present disclosure comprises a carboxypolymethylene, such as, but not limited to, those commercially available from Lubrizol Corporation of Wickliffe, Ohio under the trade name Carbopol®. Carbopol® polymers that may be present in a composition of the present disclosure in accordance with some embodiments include, but are not limited to, Carbopol® 974P NF polymer, such as Type A, Type B and/or Type C Homopolymers; Carbopol® Ultrez 10, 20, 21 NF polymer; Carbopol® 971P NF polymer; Carbopol® 980P polymer, Carbopol® ETD 2020 NF polymer, Carbopol® 71 G NF polymer, Carbopol® 981P NF polymer, Carbopol® 970P NF polymer, Carbopol® 981 P NF polymer, Carbopol® 5984P NF polymer, Carbopol® 934P NF polymer, Carbopol® 940P NF polymer, Carbopol® 941P NF polymer, Carbopol® 13242 NF polymer, Carbopol® AA-1 USP NF polymer, Carbopol® TR1 NF polymer, Carbopol® TR2 NF polymer, Lubrizol Aqua CC polymer, and SF-2 polymer, and any combination thereof.

A viscosity increasing agent may be present in a composition of the present disclosure in accordance with some embodiments. In some embodiments, a composition of the present disclosure comprises at least two viscosity increasing agents that may be the same or different. In some embodiments, a first viscosity increasing agent may be present in a composition of the present disclosure in an amount of about 0.01% to about 5% by weight of the composition or any range and/or individual value therein, such as, but not limited to, about 0.05% to about 3% or about 0.1% to about 1.5% by weight of the composition. In some embodiments, a first viscosity increasing agent is present in a composition of the present disclosure in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, or 5% by weight of the composition or any range and/or individual value therein.

Water may be present in a composition of the present disclosure in accordance with some embodiments in an amount of about 70% to about 99% by weight of the composition or any range and/or individual value therein, such as, but not limited to, about 75% to about 95% or about 80% to about 90% by weight of the composition. In some embodiments, water is present in a composition of the present disclosure in an amount of about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% by weight of the composition or any range and/or individual value therein.

In some embodiments, a composition of the present disclosure may comprise at least one polyhydric alcohol present in an amount of about 1% to about 30% by weight of the composition, at least one viscosity increasing agent present in an amount of about 0.1% to about 5% by weight of the composition, and water present in an amount of about 70% to about 99% by weight of the composition. In some embodiments, the composition may be in the form of a hydrogel. In some embodiments, the viscosity increasing agent may be a carboxypolymethylene.

A composition of the present disclosure may comprise a preservative. A preservative may be present in a composition of the present disclosure in accordance with some embodiments in an amount of about 0.01% to about 1% by weight of the composition or any range and/or individual value therein, such as, but not limited to, about 0.05% to about 1% or about 0.1% to about 1% by weight of the composition. In certain embodiments, a preservative is present in a composition of the present disclosure in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, or 1% by weight of the composition or any range and/or individual value therein. Preservatives that may be present in a composition of the present disclosure in accordance with some embodiments include, but are not limited to, sorbic acid, benzoic acid, methyl-paraben, propyl-paraben, methylchloroisothiazolinone, methylisothiazolinone, diazolidinyl urea, chlorobutanol, triclosan, benzethonium chloride, p-hydroxybenzoate, chlorhexidine, digluconate, hexadecyltrimethylammonium bromide, alcohols, benzalkonium chloride, boric acid, bronopol, butylparaben, butylene calcium acetate, calcium chloride, calcium lactate, carbon dioxide, cationic, and bentonite, cetrimide, cetylpyridinium chloride, chlorhexidine, chlorobutanol, chlorocresol, chloroxylenol, citric acid monohydrate, cresol, dimethyl ether, ethylparaben, glycerin, hexetidine, imidurea, isopropyl alcohol, lactic acid, monothioglycerol, pentetic acid, phenol, phenoxyethanol, phenylethyl alcohol, phenylmercuric acetate, phenylmercuric borate, phenylmercuric nitrate, potassium benzoate, potassium metabisulfite, potassium sorbate, propionic acid, propyl gallate, propylene glycol, sodium acetate, sodium benzoate, sodium borate, sodium lactate, sodium sulfite, sodium propionate, sodium metabisulfite, xylitol, sulphur dioxide, carbon dioxide, and any combination thereof.

A composition of the present disclosure in accordance with some embodiments may comprise a neutralizing agent. In some embodiments, a neutralizing agent may be present in a composition of the present disclosure in an amount sufficient to provide the composition with a pH of about 3 to about 8, or any range and/or individual value therein, such as, but not limited to, about 4 to about 7 or about 6 to about 7. In some embodiments, a neutralizing agent adjusts the pH of the composition. In some embodiments of the present disclosure, a neutralizing agent is present in a composition of the present disclosure in an amount sufficient for the composition to have a pH of about 3, 3.5, 4, 4.5, 5, 5.5, 6, 6.5, 7, 7.5, or 8 or any range and/or individual value therein. Neutralizing agents that may be present in a composition of the present disclosure in accordance with some embodiments include, but are not limited to, bases such as sodium hydroxide, potassium hydroxide, and mixtures thereof; acids such as hydrochloric acid, citric acid, acetic acid, and mixtures thereof sodium carbonate; trolamine; tromethamine; aminomethyl propanol; triisopropanolamine; aminomethyl propanol; tetrahydroxypropyl ethylenediamine; tetrasodium EDTA; suttocide A; and any combination thereof.

A composition of the present disclosure in accordance with some embodiments may be unbuffered or buffered. In some embodiments, a composition of the present disclosure may be unbuffered. In other embodiments, a composition of the present disclosure may be buffered. Buffers that may be present in the composition of the present disclosure include, but are not limited to, acetic acid/acetate buffers; hydrochloric acid/citrate buffers; citro-phosphate buffers; phosphate buffers; citric acid/citrate buffers; lactic acid buffers; tartaric acid buffers; malic acid buffers; glycine/HCl buffers; saline buffers such as phosphate buffered saline (PBS), Tris-buffered saline (TBS), Tris-HCl, sodium chloride, Tween buffered saline (TNT), phosphate buffered saline, Triton X-100 (PBT) and mixtures thereof; cacodylate buffers; barbital buffers; tris buffers; and any combination thereof.

In some embodiments, a composition of the present disclosure may comprise a buffering agent. In some embodiments, buffering agents include, but are not limited to, citric acid, acetic acid, lactic acid, boric acid, succinic acid, malic acid, and any combination thereof. In some embodiments, a buffering agent may be present in a composition of the present disclosure in an amount of about 0.01% to about 2% by weight of the composition or any range and/or individual value therein, such as, but not limited to, about 0.05% to about 1%, about 0.1% to about 0.5%, or about 0.1% to about 2% by weight of the composition. In some embodiments, a buffering agent is present in a composition of the present disclosure in an amount of about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% by weight of the composition or any range and/or individual value therein.

In some embodiments, a buffer is present in a composition of the present disclosure in an amount sufficient for the composition to have a pH of about 3 to about 8, or any range and/or individual value therein, such as, but not limited to, about 4 to about 7 or about 6 to about 7. In some embodiments of the present disclosure, a buffer is present in a composition of the present disclosure in an amount sufficient for the composition to have a pH of about 3, 3.5, 4, 4.5, 5, 5.5, 6, 6.5, 7, 7.5, or 8 or any range and/or individual value therein.

In some embodiments, a composition of the present disclosure may be antimicrobial. In some embodiments, a composition of the present disclosure comprises a preservative that is present in an amount sufficient to provide antimicrobial activity to the composition. In some embodiments, a composition of the present disclosure comprises at least one polyhydric alcohol present in an amount of about 1% to about 30% by weight of the composition, at least one viscosity increasing agent present in an amount of about 0.1% to about 5% by weight of the composition, water present in an amount of about 70% to about 99% by weight of the composition, and at least one preservative in an amount of about 0.01% to about 1% by weight of the composition. In some embodiments, the composition may be buffered to have a pH in a range of about 3 to about 8 or about 6 to about 8.

A composition of the present disclosure in accordance with some embodiments may have a viscosity in a range of about 5,000 cP to about 25,000 cP or any range and/or individual value therein, such as, but not limited to, about 5,000 cP to about 20,000 cP or about 7,000 cP to about 15,000 cP. In some embodiments, a composition of the present disclosure may have a viscosity of about 5,000, 5,500, 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 20,500, 21,000, 21,500, 22,000, 22,500, 23,000, 23,500, 24,000, 24,500, or 25,000 cP or any range and/or individual value therein.

A composition of the present disclosure in accordance with some embodiments may comprise an active pharmaceutical ingredient (API). Any suitable API or combinations of APIs may be included in a composition of the present disclosure. Examples of APIs include, but are not limited to, antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, antibiofilm agents, and any combination thereof. APIs include, but are not limited to, those described in International Application Publication No. WO 2013/006608. Alternatively, a composition of the present disclosure in accordance with some embodiments may not comprise an API. In some embodiments, a composition of the present disclosure does not contain a nitric oxide (NO) releasing API. In some embodiments, the composition may comprise at least one API, but the composition does not comprise an NO releasing API.

Pharmaceutical Compositions

In some embodiments, the present disclosure also provides pharmaceutical compositions that may be administered topically. In some embodiments, a pharmaceutical composition of the present disclosure may comprise a hydrophobic base and an amphiphilic compound. In some embodiments of the present disclosure, a pharmaceutical composition further comprises a moisture activated active pharmaceutical ingredient (API). In some embodiments, a pharmaceutical composition of the present disclosure may comprise an ointment, salve, cream, and/or the like.

"Hydrophobic base," as used herein, refers to a natural and/or synthetic fat, wax, oil, and/or the like. Any suitable hydrophobic base may be used in a pharmaceutical composition of the present disclosure. In some embodiments of the present disclosure, a pharmaceutical composition comprises two or more hydrophobic bases, including, but not limited to, 2, 3, 4, 5, or more hydrophobic bases. In some embodiments, hydrophobic bases include, but are not limited to, branched and unbranched hydrocarbons, branched and unbranched hydrocarbon waxes, vaseline, hydrocarbon gel, liquid paraffin, white petrolatum, petrolatum, microcrystalline wax, andelilla wax, carnauba wax, lanolin (wool wax), wool wax alcohol, esparto grass wax, cork wax, guaruma wax, rice bran wax, sugar cane wax, berry wax, ouricury wax, soy wax, jojoba oil, uropygial grease, ceresine, paraffin waxes, micro waxes, plant oils, animal oils, carnauba wax, beeswax, cacao butter, hard fat, mineral oil, vegetable oil, avocado oil, borage oil, canola oil, castor oil, chamomile oil, coconut oil, corn oil, cottonseed oil, rapeseed oil, evening primrose oil, safflower oil, sunflower oil, soybean oil, sweet almond, palm oil, palm kernel oil, *Arctium lappa* seed oil, sesame oil, borgo officialis seed oil, *Brassica campestris* oleifera oil, brevoortia oil, bubulum oil, cistus ladaniferus oil, *Elaeis guineensis* oil, almond oil, pine oil, olive oil, peanut oil, wheat germ oil, grape seed oil, thistle oil, lard, tallow, palm olein, illipe butter, shea butter, cocoa butter, kokum butter, sal butter, lecithin, japan wax lanolin, partially hydrogenated vegetable oils, hydrophobic polymers, and any combination thereof.

In some embodiments of the present disclosure, a hydrophobic base may comprise a hydrophobic polymer. Any suitable hydrophobic polymer may be used in a pharmaceutical composition of the present disclosure. In some embodiments, hydrophobic polymers include, but are not limited to hydrocarbon polymers and/or co-polymers, aromatic polyurethanes, silicone rubber, polysiloxanes, polycaprolactone, polycarbonate, polyvinyl chloride, polyethylene, poly-L-lactide, poly-DL-glycolide, polyetheretherketone (PEEK), polyamide, polyimide and polyvinyl acetate. In particular embodiments of the present disclosure, a pharmaceutical composition of the present disclosure comprises one or more hydrocarbon polymers and/or co-polymers. In some embodiments, a pharmaceutical composition of the present disclosure comprises one or more hydrocarbon polymers and/or co-polymers, such as, but not limited to, those commercially available from Calumet Specialty Products Partners of Indianapolis, Ind. under the trademark Versagel® and/or those commercially available from Croda International Plc of East Yorkshire, United Kingdom under the trade name Crodabase SQ.

In some embodiments of the present disclosure, a hydrophobic polymer may act as a thickening and/or gelling agent in a pharmaceutical composition. In some embodiments, a hydrophobic polymer may act as a visco-elastic substance and may retain the composition at the site of application, along with any compounds dispersed therein (e.g., an API, etc.). A hydrophobic polymer may be present in a pharmaceutical composition of the present disclosure at a concentration from about 30% to about 60% by weight or any range therein, such as, but not limited to, from about 35% to about 55% by weight or about 40% to about 50% by weight.

In some embodiments of the present disclosure, a hydrophobic base comprises one or more plant and/or mineral oils. Any suitable oil may be used in the pharmaceutical compositions of the present disclosure. In some embodiments mineral oils include, but are not limited to, light mineral oil, white mineral oil, paraffinic oils, naphthenic oils, aromatic oils, and any combination thereof. An oil (e.g., plant and/or mineral oil) may be present in a pharmaceutical composition of the present disclosure in accordance with some embodiments at a concentration from about 1% to about 30% by weight or any range therein, such as, but not limited to, from about 5% to about 20% by weight or about 5% to about 15% by weight.

In some embodiments of the present disclosure, a hydrophobic base, such as, but not limited to, an oil (e.g., a plant and/or mineral oil), may be used to tune the viscosity and/or spreadability of the pharmaceutical composition. In some embodiments, a low viscosity hydrophobic base, such as light mineral, may be used to thin (i.e., reduce the viscosity) a pharmaceutical composition, such as, a pharmaceutical composition comprising a high viscosity hydrophobic base. This may enable the application of a pharmaceutical composition of the present disclosure in accordance with some embodiments over a wide area, and may serve to maintain any compounds dispersed therein (e.g., an API, etc.) at the site of application. In some embodiments of the present disclosure, a hydrophobic base comprises a mineral oil and a hydrophobic polymer.

A hydrophobic base may be present in a pharmaceutical composition of the present disclosure in accordance with some embodiments at a concentration from about 35% to about 90% by weight or any range therein, such as, but not limited to, from about 40% to about 80% by weight or about 50% to about 70% by weight. In some embodiments of the present disclosure, a hydrophobic base is present in a pharmaceutical composition of the present disclosure at a concentration from about 45% to about 55% by weight.

"Amphiphilic compound," as used herein, refers to a compound comprising hydrophilic and hydrophobic properties. An amphiphilic compound may comprise two or more compounds, each of which may provide the hydrophilic property and/or the hydrophobic property. In some embodiments, the amphiphilic compound comprises one compound having hydrophilic and hydrophobic properties. In some embodiments of the present disclosure, an amphiphilic compound may absorb moisture without substantially absorbing vaporous moisture. The absorption of moisture may allow for activation of a moisture activated pharmaceutical ingredient in a pharmaceutical composition of the present disclosure upon contact with the moisture, but not upon contact with vaporous moisture. "Substantially absorbing" (and grammatical variations thereof), as used herein, means that the amount of vaporous moisture absorbed is more than 2% by weight of an amphiphilic compound. Thus, an amphiphilic compound of the present disclosure absorbs vaporous moisture by less than about 2%, 1.5%, 1%, 0.5%, 0.25% by weight of an amphiphilic compound or any range therein. In some embodiments of the present disclosure, an amphiphilic compound may prevent and/or minimize a pharmaceutical composition of the present disclosure from substantially absorbing vaporous moisture, thereby moisture may be present in a pharmaceutical composition of the present disclosure by less than about 2%.

"Moisture," as used herein, refers to a liquid, such as, but not limited to, bodily fluid such as, but not limited to, blood, sweat, mucus, saliva, sebum, tears, exudate, and/or vaginal secretions; water; deoxygenated water; saline solutions; acidic or alkaline buffer solutions; and/or any combination thereof "Vaporous moisture," as used herein, refers to moisture in the gas phase. In some embodiments, vaporous moisture, includes, but is not limited to, water vapor. Thus, in some embodiments of the present disclosure, an amphiphilic compound may prevent and/or minimize the absorption of water vapor, thereby, when the API comprises a moisture activated pharmaceutical ingredient, the API in a pharmaceutical composition of the present disclosure is not activated by the vaporous moisture (e.g., water vapor). In contrast, an amphiphilic compound may absorb and/or allow moisture (e.g., water, a bodily fluid, etc.) to be absorbed when a pharmaceutical composition of the present disclosure is contacted with the moisture, thereby, activating the API when the API comprises a moisture-activated API.

In some embodiments of the present disclosure, an amphiphilic compound absorbs water vapor by less than about 2% by weight or about 1% by weight. In some embodiments, this may minimize and/or prevent a pharmaceutical composition of the present disclosure from absorbing water vapor and thus water may be present in a pharmaceutical composition of the present disclosure by less than about 2% by weight or about 1% by weight water. In some embodiments of the present disclosure, an amphiphilic compound absorbs less than about 0.5% by weight water vapor and thus a pharmaceutical composition of the present disclosure may comprise less than about 0.5% by weight water.

In some embodiments, an amphiphilic compound may have a hydrophilic-lipophilic balance (HLB) value of 12 to 20 or any range therein, such as, but not limited to, 15 to 20 or 18 to 20. In some embodiments of the present disclosure, an amphiphilic compound comprises a HLB value of 19.

In some embodiments, amphiphilic compounds include, but are not limited to, fatty acid esters. In some embodiments, one or more fatty acid ester(s) may be present in the pharmaceutical compositions of the present disclosure, including, without limitation, 2, 3, 4, or more fatty acid esters. In some embodiments, fatty acid esters include, but are not limited to, C6-C22 alkyl and/or alkenyl fatty acid esters such as methyl laurate, ethyl laurate, ethyl myristate, ethyl palmitate, ethyl linoleate, propyl isobutyrate, isopropyl laurate, isopropyl myristate, isopropyl palmitate, oleyl myristate, oleyl stearate, and oleyl oleate; ether-esters such as fatty acid esters of ethoxylated fatty alcohols; polyhydric alcohol esters such as ethylene glycol mono- and di-fatty acid esters, diethylene glycol mono- and di-fatty acid esters; polyethylene glycol (6-2000) fatty acid mono- and/or diesters such as PEG-6-laurate, PEG-6-stearate, PEG-8-dilaurate, PEG-8-distearate, etc.; polyethylene glycol glycerol fatty acid esters such as PEG-20-glyceryl laurate, PEG-20-glyceryl stearate, and PEG-20-glyceryl oleate; propylene glycol mono- and di-fatty acid esters; polypropylene glycol 2000 monooleate; polypropylene glycol 2000 monostearate; ethoxylated propylene glycol monostearate; glyceryl mono- and di-fatty acid esters; polyglycerol fatty acid esters such as polyglyceryl-10 laurate, etc.; ethoxylated glyceryl monostearate; 1,3-butylene glycol monostearate; 1,3-butylene glycol distearate; polyoxyethylene polyol fatty acid ester; sorbitan fatty acid esters including sorbitan trioleate and sorbitan monolaurate; polyethylene glycol sorbitan fatty acid esters such as PEG-6 sorbitan monooleate; polyoxyethylene sorbitan fatty acid esters, including, without limitation, polyoxyethylene (20) sorbitan monolaurate; sucrose fatty acid esters such as saccharose monopalmitate and saccharose monostearate; wax esters such as beeswax, spermaceti, myristyl myristate, stearyl stearate and arachidyl behenate; polyethylene glycol alkyl ethers such as PEG-10 oleyl ether or PEG-9 cetyl ether; polyethylene glycol alkyl phenols such as PEG-10-100 nonyl phenol; polyoxyethylene-polyoxypropylene block copolymers such as poloxamer 188; sterol esters such as cholesterol fatty acid esters, and any combination thereof.

In some embodiments, a fatty acid ester may comprise a polyethylene glycol (PEG) glyceride. In some embodiments, the polyethylene glycol portion of a PEG glyceride may provide the hydrophilic property of an amphiphilic compound and may include, but is not limited to, PEG 5-1000 or any range therein, and any combination thereof. In some embodiments, the glyceride portion of a PEG glyceride may provide the hydrophobic property of an amphiphilic compound and may include, but is not limited to, a natural and/or hydrogenated oil, such as but not limited to, castor oil, hydrogenated castor oil, vitamin A, vitamin D, vitamin E, vitamin K, a plant oil (e.g., corn oil, olive oil, peanut oil, palm kernel oil, apricot kernel oil, almond oil, etc.), and any combination thereof. In some embodiments, polyethylene glycol (PEG) glycerides include, but are not limited to, PEG-20 castor oil, PEG-20 hydrogenated castor oil, PEG-20 corn glycerides, PEG-20 almond glycerides; PEG-23 trioleate, PEG-40 palm kernel oil, PEG-8 caprylic/capric glycerides, PEG-6 caprylic/capric glycerides, lauroyl macrogol-32 glyceride, stearoyl macrogol glyceride, tocopheryl PEG-1000 succinate, and any combination thereof. In some embodiments of the present disclosure a fatty acid ester comprises a PEG 5-30 (i.e., PEG 5, 6, 7, 8, 9, 10, etc.) and a caprylic/capric glyceride. In some embodiments of the present disclosure, a pharmaceutical composition comprises a PEG-5-caprylic/capric glyceride, a PEG-6-caprylic/capric glyceride, a PEG-7-caprylic/capric glyceride, and/or a PEG-8-caprylic/capric glyceride. In some embodiments of the present disclosure, a pharmaceutical composition of the present disclosure comprises one or more fatty acid esters such as, but not limited to, those commercially available from Sasol of Hamburg, Germany under the trademark SOFTIGEN®.

In some embodiments, an amphiphilic compound may be present in a pharmaceutical composition of the present disclosure at a concentration from about 1% to about 30% by weight or any range therein, such as, but not limited to, from about 2% to about 20% by weight or about 5% to about 15% by weight. In some embodiments of the present disclosure, an amphiphilic compound is present in a pharmaceutical composition of the present disclosure at a concentration of about 10% by weight.

In some embodiments, a pharmaceutical composition of the present disclosure may further comprise one or more excipients. Excipients for use in pharmaceutical compositions in accordance with some embodiments of the present disclosure are well-known in the art and examples may be found in the Handbook of Pharmaceutical Excipients (Rowe, R. C. et al., APhA Publications; 5th ed., 2005). Classes of excipients may include, but are not limited to, an emollient, a humectant, a cosolvent, a pH modifier, a water repelling agent, an anti-foaming agent, a surfactant, a solubilizer, a wetting agent, a penetration enhancer, an antioxidant, and/or a solvent. The excipients may be present in a pharmaceutical composition of the present disclosure at any suitable concentration.

In some embodiments of the present disclosure, a pharmaceutical composition may further comprise a cosolvent. A cosolvent may be present in a pharmaceutical composition of the present disclosure at a concentration from about 1% to about 30% by weight or any range therein, such as, but not limited to, from about 2% to about 20% by weight or about 5% to about 15% by weight. In some embodiments of the present disclosure, a cosolvent is present in a pharmaceutical composition of the present disclosure at a concentration from about 10% to about 15% by weight.

In some embodiments, cosolvents include, but are not limited to, a fatty acid ester, propylene glycol, glycerol, polyethylene glycol. In some embodiments of the present disclosure, a cosolvent may comprise a neutral oil. In some embodiments of the present disclosure, a cosolvent comprises a caprylic and/or capric triglyceride such as, but not limited to, those commercially available from Sasol of Hamburg, Germany under the trademark MIGLYOL®.

The pharmaceutical compositions of the present disclosure in accordance with some embodiments may comprise a humectant. Any suitable humectant or combination of humectants may be used herein. In some embodiments, a humectant may be present in a pharmaceutical composition of the present disclosure at a concentration from about 1% to about 25% by weight or any range therein, such as, but not limited to, from about 2% to about 20% by weight or about 5% to about 15% by weight. In some embodiments of the present disclosure, a humectant is present in a pharmaceutical composition of the present disclosure at a concentration from about 10% to about 15% by weight.

In some embodiments, humectants include, but are not limited to, glycols, such as a polyhydric alcohol, diethylene glycol monoethyl ether and methoxy polyethylene glycol; glycerols such as propylene glycol, glycerol, isopropanol, ethanol, ethylene glycol, polyethylene glycol, ethoxydiglycol, or mixtures thereof; sugar polyols, such as sorbitol, xylitol and maltitol; polyols such as polydextroses; dimethyl isosorbide; quillaia; urea; and any combination thereof. In particular embodiments of the present disclosure, a humectant comprises an alkylene glycol, such as hexylene glycol, butylene glycol, pentylene glycol, and any combination thereof.

Oral Care Compositions

In some embodiments, the photocatalyzable composition may be an oral care composition to be topically applied to the mucosal tissue of the oral cavity, to the gingival tissue of the oral cavity, to the surface of the teeth or any combination thereof. Examples of oral conditions that such photocatalyzable compositions address include, but are not limited to, appearance and structural changes to teeth, whitening, stain bleaching, stain removal, plaque removal, tartar removal, cavity prevention and treatment, inflamed and/or bleeding gums, mucosal wounds, lesions, ulcers, aphthous ulcers, cold sores and tooth abscesses, oral malodor, dental erosion, gingivitis, and/or periodontal disease. Oral conditions are further described in WO 02/02096A2.

In some embodiments, the photocatalyzable composition may include one or more oral care actives. In some embodiments, the oral care active can be any material that is generally recognized as safe for use in the oral cavity that provides changes to the overall health of the oral cavity, and specifically the condition of the oral surfaces the oral care active contacts. In some embodiments, the photocatalyzable composition can comprise one or multiple oral care additives.

In some embodiments, it is also contemplated that a single oral care product can comprise multiple photocatalyzable compositions, each of which comprises one or more oral care additives. Some oral care additives that are suitable for use in the photocatalyzable composition are discussed more fully below.

In some embodiments, the photocatalyzable composition may include one or more gelling agents, which may also act as an adhesive agent to adhere the photocatalyzable composition to the plurality of teeth. In some embodiments, the concentration of the gelling agent may be greater than about 2, 4, 6, 8, 10, 15, 20, 30, 40, 50, 60 or less than about 80, 70, 60, 50, 40, 30, or 20 percent by weight of the photocatalyzable composition.

Suitable gelling agents and/or adhesion agents useful in some embodiments of the present disclosure are described in U.S. Pat. Nos. 6,649,147; 6,780,401; 2004/0102554; 2005/0089819; 2003/0152528; 6,419,906; and 2005/0100515. Some of the gelling agents or adhesion agents that may be used in some embodiments of the present disclosure may include silicone, polyethylene oxide, polyvinyl alcohol, poly alkyl vinyl ether-maleic acid copolymer (PVM/MA copolymer) such as, Gantrez AN 119, AN 139, and S-97, polyvinyl alcohol, polyacrylic acid, Poloxamer 407 (Pluronic), polyvinylpyrrolidone-vinyl acetate copolymer (PVP/VA copolymer), such as Luviskol VA, and Plasdone S PVP/VA, polyvinyl pyrrolidone (PVP, e.g., K-15 to K-120), Polyquaternium-11 (Gafquat 755N), Polyquaternium-39 (Merquat plus 3330), carbomer or carboxypolymethylene (Carbopol), hydroxypropyl methyl cellulose, hydroxyethyl cellulose, hydroxypropyl cellulose, carboxymethyl cellulose, gelatin and alginate salt such as sodium alginate, natural gums such as gum karaya, xanthan gum, Guar gum, gum arabic, gum tragacanth, and mixtures thereof.

In some embodiments, a humectant or plasticizer may be included in the photocatalyzable composition, including glycerin, sorbitol, polyethylene glycol, propylene glycol, and other edible polyhydric alcohols. In some embodiments, the humectants may be present between about 10% to about 95%, or between about 50% and about 80%, by weight of the photocatalyzable composition. In some embodiments, a photocatalyzable composition can also include flavoring agents, sweetening agents, opacifiers, and coloring agents.

In some embodiments, the photocatalyzable composition of the present disclosure may comprise a non-photocatalyzable anti-tartar agent. In some embodiments, anti-tartar actives known for use in dental care products include phosphates. In some embodiments, phosphates include pyrophosphates, polyphosphates, polyphosphates, and mixtures thereof. Pyrophosphates are known for use in dental care products. Pyrophosphate ions that are delivered to the teeth derive from pyrophosphate salts. The pyrophosphate salts useful in the compositions of the present disclosure in accordance with some embodiments include, but are not limited to, the dialkali metal pyrophosphate salts, tetra-alkali metal pyrophosphate salts, and mixtures thereof. In some embodiments, disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their unhydrated as well as hydrated forms are utilized. In some embodiments, the photocatalyzable compositions of the present disclosure comprise from about 0.5% to about 5% of a pyrophosphate by weight of the photocatalyzable composition. In other embodiments, the photocatalyzable composition comprises from about 0.5% to about 3% of a pyrophosphate by weight of the photocatalyzable composition.

The pyrophosphate salts in accordance with some embodiments of the present disclosure are described in more detail in Kirk & Othmer, Encyclopedia of Chemical Technology, Third Edition, Volume 17, Wiley-Interscience Publishers (1982), incorporated herein by reference in its entirety, including all references incorporated into Kirk & Othmer. In some embodiments, anticalculus phosphates may be included in the photocatalyzable compositions of the present disclosure. In some embodiments, the anticalculus phosphates include, but are not limited to, potassium and sodium pyrophosphates; sodium tripolyphosphate; diphosphonates, such as ethane-1-hydroxy-1,1-diphosphonate, 1-azacycloheptane-1,1-diphosphonate, and linear alkyl diphosphonates; linear carboxylic acids; and sodium zinc citrate.

Actives that may be used in place of or in combination with the pyrophosphate salt in accordance with some embodiments of the present disclosure include such known materials as synthetic anionic polymers including polyacrylates and copolymers of maleic anhydride or acid and methyl vinyl ether (e.g., Gantrez), polyamino propane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof. Other anti-tartar actives include, without limitation, sodium hexametaphosphate.

The photocatalyzable compositions of the present disclosure may also comprise a non-photocatalyzable anti-caries agent. Fluoride ion sources are well known for use in oral care compositions as anticaries actives. In some embodiments, fluoride ions are contained in a number of oral care compositions for this purpose, such as, for example, toothpastes.

Application of fluoride ions to dental enamel serves to protect teeth against decay. A wide variety of fluoride ion-yielding materials can be employed as sources of soluble fluoride in the photocatalyzable compositions of the present disclosure. Fluoride ion sources for use in some embodiments of the present disclosure include stannous fluoride, monofluorophosphate, sodium fluoride, potassium fluoride, and ammonium fluoride. In some embodiments, the instant photocatalyzable compositions provide from about 50 ppm to about 10,000 ppm, or from about 100 to about 3000 ppm of fluoride ions in the aqueous solutions that contact dental surfaces when used with the strip of material used in the mouth. In some embodiments, other anti-caries actives include xylitol.

The photocatalyzable composition of the present disclosure in accordance with some embodiments of the present disclosure may comprise a non-photocatalyzable antimicrobial agent. Non-photocatalyzable antimicrobial agents suitable for use in some embodiments of the present disclosure may include, but are not limited to, 5-chloro-2-(2,4-dichlorophenoxy)-phenol, commonly referred to as triclosan, and described in The Merck Index, 11th ed. (1989); phthalic acid and its salts; substituted monoperthalic acid and its salts and esters; magnesium monoperoxy phthalate, chlorhexidine (Merck Index, no. 2090), alexidine (Merck Index, no. 222); hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024); tetradecyl pyridinium chloride (TPC); N-tetradecyl-4-ethylpyridinium chloride (TDEPC); octenidine; delmopinol, octapinol, and other piperidino derivatives; niacin preparations; zinc/stannous ion actives; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol), metals or metal ions (e.g., silver, copper, zinc, etc) and mixtures thereof methyl salicylate; chlorite and metal salts of chlorite and mixtures of all of the above.

The photocatalyzable composition of the present disclosure in accordance with some embodiments may comprise a non-photocatalyzable anti-inflammatory or non-photocatalyzable anti-sensitivity agent. In some embodiments, anti-inflammatory agents may include, but are not limited to, non-steroidal anti-inflammatory actives or NSAIDs such as ketorolac, flurbiprofen, ibuprofen, naproxen, indomethacin, aspirin, ketoprofen, piroxicam, and meclofenamic acid.

Anti-sensitivity agents suitable for use in some embodiments of the present disclosure can include potassium nitrate, clove oil (Eugenol) and other herbal or flavor actives/agents.

In some embodiments, nutrients may improve the condition of the oral cavity and can be included in the photocatalyzable compositions of the present disclosure. In some embodiments, the photocatalyzable composition of the present disclosure may comprise a non-photocatalyzable nutrient such as minerals, vitamins, oral nutritional supplements, enteral nutritional supplements, and mixtures thereof.

Minerals that can be included with the photocatalyzable compositions of the present disclosure include, but are not limited to, calcium, phosphorus, fluoride, zinc, manganese, potassium, and mixtures thereof. These minerals are disclosed in Drug Facts and Comparisons (loose leaf drug information service), Wolters Kluwer Company, St. Louis, Mo., COPYRIGHT. 1997, pp 10-17, which is incorporated herein by reference in its entirety.

In some embodiments, vitamins can be included with minerals or used separately. Vitamins that may be included in some embodiments of the compositions of the present disclosure, include, without limitation, Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluwer Company, St. Louis, Mo., COPYRIGHT. 1997, pp. 3-10.

Oral nutritional supplements that can be included with the photocatalyzable compositions of the present disclosure include, but are not limited to, amino acids, lipotropics, fish oil, and mixtures thereof, as disclosed in Drug Facts and Comparisons (loose leaf drug information service), Wolters Kluwer Company, St. Louis, Mo., COPYRIGHT. 1997, pp. 54-54e. In some embodiments, amino acids include, but, are not limited to L-Tryptophan, L-Lysine, Methionine, Threonine, Levocarnitine or L-carnitine, and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid, and docosahexaenoic acid.

Enteral nutritional supplements that can be included with the photocatalyzable compositions of the present disclosure include but are not limited to protein products, glucose polymers, corn oil, safflower oil, and medium chain triglycerides, as disclosed in Drug Facts and Comparisons (loose leaf drug information service), Wolters Kluwer Company, St. Louis, Mo., COPYRIGHT. 1997, pp. 55-57.

pH Adjustment Agent
Alkaline Material

In some embodiments, an alkaline material may be present to trim the pH and/or maintain the pH of the compositions according to the present disclosure. In some embodiments, the amount of alkaline material is from about 0.001% to about 20% by weight of the composition. In some embodiments, the amount of alkaline material is from about 0.01 to about 10% by weight of the composition. In some embodiments, the amount of alkaline material is from about 0.05% to about 3% by weight of the composition.

Examples of the alkaline material are sodium hydroxide, potassium hydroxide, and/or lithium hydroxide, and/or the alkali metal oxide, such as sodium and/or potassium oxide, or mixtures thereof.

Acid

The photocatalyzable composition of the present disclosure in accordance with some embodiments may comprise an acid. Any acid known to those skilled in the art may be used herein. In some embodiments, the composition herein may comprise up to about 20%, from about 0.1% to about 10%, from about 0.1% to about 5%, or from about 0.1% to about 3%, by weight of the total composition of an acid.

Suitable acids for use in accordance with some embodiments of the present disclosure are selected from the group consisting of a mono- and poly-carboxylic acid or a mixture thereof; a percarboxylic acid or a mixture thereof; and a substituted carboxylic acid or a mixture thereof; and mixtures thereof. Carboxylic acids useful herein include $C_{1-6}$ linear or at least about 3 carbon containing cyclic acids. The linear or cyclic carbon-containing chain of the carboxylic acid may be substituted with a substituent group selected from the group consisting of hydroxyl, ester, ether, aliphatic groups having from about 1 to about 6, or from about 1 to about 4 carbon atoms, and mixtures thereof.

Suitable mono- and poly-carboxylic acids are selected from the group consisting of citric acid, lactic acid, ascorbic acid, isoascorbic acid, tartaric acid, formic acid, maleic acid, malic acid, malonic acid, propionic acid, acetic acid, dehydroacetic acid, benzoic acid, hydroxy benzoic acid, and mixtures thereof.

Suitable percarboxylic acids are selected from the group consisting of peracetic acid, percarbonic acid, perboric acid, and mixtures thereof.

Preferred acids for use herein are selected from the group consisting of lactic acid, citric acid, and ascorbic acid, and mixtures thereof.

Suitable acids are commercially available from JBL, T&L, or Sigma. Lactic acid is commercially available from Sigma and Purac.

Methods of Use

The present disclosure further provides methods of using the compositions of the present disclosure to provide benefits.

The present disclosure further provides a method for treating wounds comprising contacting the wound in need of treatment with the photocatalyzable composition, described in detail above, having at least 0.001 ppm of an activator, described in detail above, followed by exposing the wound to a source of light.

The present disclosure also provides a method of treating skin comprising contacting the skin in need of treatment with the photocatalyzable composition, described in detail above, having at least 0.001 ppm of an activator, described in detail above, followed by exposing the wound to a source of light.

The present disclosure further encompasses a method of disinfecting a surface. In some embodiments, the method comprises the steps of contacting the surface with a composition of the present disclosure and exposing the composition to light. In some embodiments, the light has a wavelength greater than about 350 nm.

The present disclosure further encompasses a method of removing biofilm from a surface. In some embodiments, the method comprises the steps of contacting the biofilm with a composition of the present disclosure and exposing the composition to light. In some embodiments, the light has a wavelength greater than about 350 nm.

The present disclosure further provides a method for treating or cleaning an oral cavity, including teeth or dentures (inside or outside the oral cavity). In some embodiments, the method comprises contacting the oral cavity (including teeth or dentures) in need of treatment or cleaning with the photocatalyzable composition, described in detail above, having at least 0.001 ppm of a photoactivator, described in detail above, followed by exposing the teeth or dentures to a source of light having a minimal wavelength range of greater than about 300 nanometers. In some embodiments, the source of light has a minimal wavelength range of greater than about 350 nanometers. In some embodiments, the source of light has a minimal wavelength range of up to about 550 nanometers. In some embodiments, the source of light has a minimal wavelength range of up to about 500 nanometers.

Acne Composition

In some embodiments of the present disclosure, at least one photocatalyzable composition is applied to the skin in a pharmaceutically acceptable composition for the treatment of acne vulgaris. A "pharmaceutically acceptable composition," as defined herein, refers to a composition that is suitable for application to a subject, such as a human, without undue side effects such as toxicity or irritation to the skin. Undue side effects are those that render the composition unsuitable for application to a subject because the harm from the side effects outweigh the benefits of the composition. In some embodiments, pharmaceutically acceptable compositions include at least one photocatalyzable composition; optionally, at least one additional therapeutic agent; and at least one pharmaceutically acceptable excipient.

The photocatalyzable composition of the present disclosure may be present in pharmaceutically acceptable compositions according to embodiments of the present disclosure at any suitable concentration. In some embodiments, the concentration of the photocatalyzable composition ranges from 0.1% to 90% w/w, 0.5% to 50% w/w, and 1% to 30% w/w in the composition.

As described above, in some embodiments, pharmaceutically acceptable compositions include at least one additional therapeutic agent, such as those that have antimicrobial, anti-inflammatory, pain-relieving, immunosuppressant, or vasodilating properties. In some embodiments, other anti-acne therapeutic agents, such as retinoids, may also be included in the compositions according to an embodiment of the present disclosure.

In some embodiments, the pharmaceutically acceptable compositions of the present disclosure may be present in any physical form, including, without limitation, ointments, creams, milks, pomades, powders, impregnated pads, solutions, gels, sprays, lotions, or suspensions. In some embodiments, the pharmaceutically acceptable compositions of the present disclosure may also be in the form of suspensions of microspheres or nanospheres, or of lipid or polymeric vesicles, or of polymeric patches and hydrogels for controlled release. In some embodiments, the pharmaceutically acceptable compositions of the present disclosure may be in anhydrous form, in aqueous form, or in the form of an emulsion (e.g., oil in water or water in oil emulsions).

As used herein, the term "excipient" refers to inert constituents of pharmaceutically acceptable compositions. The term "inert" indicates that such constituents are not therapeutic agents such as the photocatalyzable composition or other antimicrobial compounds, anti-inflammatory agents, pain-relievers, immunosuppressants, and vasodilators. However, as one of ordinary skill in the art will understand, the excipients may provide beneficial or therapeutic action to the skin (e.g., moisturize.) that may directly affect the acne. The excipients may also indirectly affect the treatment of acne by affecting the activity of the photocatalyzable composition or other therapeutic agents within the compositions.

Excipients for use in the compositions of the present disclosure in accordance with some embodiments are well-known in the art and examples may be found in the Handbook of Pharmaceutical Excipients (Rowe, R. C. et al., APhA Publications; 5th ed., 2005). In some embodiments, excipients may include talc, calcium carbonate, calcium phosphate, magnesium stearate, waxes, various sugars and types of starch, polymers, gels, emollients, thickening agents, rheology modifiers, humectants, glycerol, organic basic compounds, cellulose derivatives, gelatin, vegetable oils, polyethylene glycols, and solvents. In some embodiments, examples of rheology modifiers include Carbopol, C26-28 alkyl dimethicone, C26-28 alkyl methicone, polymethylsilsesquioxane, trimethylsiloxysilicate, crosspolymers of cyclopentasiloxane and dimethicone/vinyl trimethylsiloxysilicate, and mixtures thereof. In some embodiments, examples of emollients include glycerine, pentylene glycol, sodium pyrrolidone carboxylic acid, lanolin, saccharide isomerate, stearoxy dimethicone, stearyl dimethicone, and mixtures thereof. Emollients may be useful to prevent stratum corneum dehydration occurring due to the use of anhydrous solvents in the compositions of the present disclosure. Examples of organic bases include, without limitation, methanolamines, triethanolamines, Trisamino, AMP-95; AmP-Ultra PC 2000, triisopropanolamine, diisopropanolamine, Neutrol TE, Ethomeen, and mixtures thereof. In some embodiments, the organic base may render the pH of the medicament basic or neutral, and may directly affect the release of NO from the NO-releasing compounds that include diazeniumdiolate NO donor groups by slowing donor decomposition with increasing alkalinity.

In some embodiments, excipients include, without limitation, water-soluble porogens. A water-soluble porogen is an additive that may facilitate water uptake and diffusion into the pharmaceutically acceptable composition. Any suitable porogen may be used herein, but in some embodiments, the porogen may include sodium chloride, sucrose, glucose, lactose, sorbitol, xylitol, polyethylene glycol, polyvinylpyrrolidone, polyvinyl alcohol, or mixtures thereof. Electrolytes, such as sodium chloride, may also be added as excipients.

In some embodiments, polymers may also act as excipients. In some embodiments, polymers include hydrophilic polyurethanes, hydrophilic polyacrylates, co-polymers of carboxymethylcellulose and acrylic acid, N-vinylpyrrolidone, poly(hydroxy acids), polyanhydrides, polyorthoesters, polyamides, polycarbonates, polyalkylenes (e.g., polyethylene and polypropylene), polyalkylene glycols (e.g., poly(ethylene glycol)), polyalkylene oxides (e.g., polyethylene oxide), polyalkylene terephthalates (e.g., polyethylene terephthalate), polyvinyl alcohols, polyvinyl ethers, polyvinyl esters, polyvinyl halides (e.g., poly(vinyl chloride)), polyvinylpyrrolidone, polysiloxanes; poly(vinyl acetates), polystyrenes, polyurethane copolymers, cellulose, derivatized celluloses, alginates, poly(acrylic acid), poly(acrylic acid) derivatives, acrylic acid copolymers, methacrylic acid, methacrylic acid derivatives, methacrylic acid copolymers, poly(butyric acid), poly(valeric acid), poly(lactide-co-caprolactone), copolymers thereof, and blends thereof.

In some embodiments of the present disclosure, the polymers may be superabsorbent polymers (SAPs). A polymer is considered superabsorbent, as defined per IUPAC, as a polymer that can absorb and retain extremely large amounts of water relative to its own mass. SAPs may absorb water up to 500 times their own weight and may swell up to 1000-times their original volume. In some embodiments, SAPs include sodium polyacrylate, the polyurethane Tecophilic TG-2000, and polymers prepared by the use of polyacrylamide copolymer, ethylene maleic anhydride copolymer, cross-linked carboxy-methyl-cellulose, polyvinyl alcohol copolymers, polyvinylpyrrolidone, and cross-linked polyethylene oxide. In some embodiments, the SAP may absorb water from the skin, thereby causing NO to release from the NO-releasing compounds.

In some embodiments of the present disclosure, polymers that are relatively hydrophobic may be used. Any suitable hydrophobic polymer may be used. However, polymers that are relatively hydrophobic include, without limitation, aromatic polyurethanes, silicone rubber, polysiloxanes, polycaprolactone, polycarbonate, polyvinyl chloride, polyethylene, poly-L-lactide, poly-DL-glycolide, polyetheretherketone (PEEK), polyamide, polyimide, and polyvinyl acetate. In some embodiments, a hydrophobic gel-base and/or rheology modifier may be used herein.

In some embodiments of the present disclosure, notably in gels, the polymers may act as thickening agents in the medicaments. In some embodiments, the polymeric portion of the gel may act as a visco-elastic substance and may retain the gel at the site of application, along with the NO-releasing compounds dispersed therein.

In some other embodiments, notably in gels and ointments, a medicament that includes a polymer may have spreadability such that it forms a thin film when applied on the skin surface. In some embodiments, a film may enable the application of the contained NO-releasing compounds over a wide area, and may serve to maintain the NO-releasing compounds on the affected area of the skin.

In some embodiments, other excipients may include various ionic or non-ionic compounds to maintain stability of the compositions of the present disclosure, thereby protecting from the de-emulsification, settling, agglomeration or degradation of the composition constituents that may reduce its therapeutic or aesthetic value.

Examples of ionic compounds may include, without limitation, salts such as sodium chloride, potassium chloride; cationic, anionic or zwitterionic surfactants such as sodium dodecyl sulfate (SDS), perfluorocetanoate (PFOA), perfluorooctanesulfonate (PFOS), ammonium lauryl sulfate (ALS), sodium lauryl ether sulfate (SLES), alkyl benzene sulfonate, cetyltrimethylammonium bromide (CTAB), cetylpyridinium chloride (CPC), polyethoxylated tallow amine (POEA), benzalkonium chloride (BAC), benzethonium chloride, dodecyl betaine, cocamidopropyl betaine and cocoamphoglycinate.

Examples of non-ionic compounds that may act as excipients include, without limitation, non-ionic surfactants such as Pluronic, Tween, AMP, and Brij family of surfactants; and surfactants derived from biological sources, e.g., natural or semi-synthetic surfactants, such as oleic acid, sorbitan trioleate, sorbitan monooleate, lecithin, cocamide MEA, cocamide DEA, and cocamidopropyl betaine. In some embodiments, surfactants (both ionic and non-ionic) may reduce the interfacial surface energy and may facilitate spreading of the ointment or liquid over a wider area.

In some embodiments of the present disclosure, solvent excipients may be used as a carrier vehicle for the photocatalyzable composition and other excipients. The polymer chains may interact with the solvent and undergo swelling to form a network that may impart visco-elastic properties to the medicament. In some embodiments of the medicament, the solvent may evaporate upon application, leaving a residual film of the polymer along with the entrapped photocatalyzable composition.

Examples of solvent excipients include dimethyl isosorbide, propylene glycol, glycerol, isopropanol, ethanol, ethylene glycol, polyethylene glycol, ethoxydiglycol, or mixtures thereof. Solvent excipients that may be useful in the compositions of the present disclosure may include isododecane, isodecyl neopentanoate, butylene glycol, pentylene glycol, hexylene glycol, methoxypolyethylene glycol, cyclopentasiloxane, cyclotetrasiloxane, dimethicone, caprylyl methicone, or mixtures thereof.

In addition to the NO-releasing molecules, excipients, and other therapeutic agents, the pharmaceutically acceptable compositions of the present disclosure may also include other compounds that improve the organoleptic properties of such composition. Examples of such compounds include perfumes, dyes and colorants; chelating agents, including, but not limited, to EDTA, EGTA, CP94, citric acid; preservatives including, but not limited to, quaternary ammonium compounds, such as benzalkonium chloride, benzethonium chloride, cetrimide, dequalinium chloride, and cetylpyridinium chloride; mercurial agents, such as phenylmercuric nitrate, phenylmercuric acetate, and thimerosal; alcoholic agents, for example, chlorobutanol, phenylethyl alcohol, and benzyl alcohol; antibacterial esters, for example, esters of para-hydroxybenzoic acid; and other antimicrobial agents such as chlorhexidine, chlorocresol, benzoic acid, and polymyxin.

As discussed above, according to some embodiments of the present disclosure, methods of treating acne vulgaris of a subject by applying the photocatalyzable composition of the present disclosure to the skin are provided. Decrease of acne may be detected by a visual reduction in the amount or severity of the acne and/or by decrease in pain or discomfort associated with the acne, as identified by the subject.

In some embodiments, the photocatalyzable composition of the present disclosure in a pharmaceutically acceptable composition according to embodiments of the present disclosure may be applied topically to the skin of the subject. Any portion of the subject's skin may be treated. However, in some embodiments, the subject's face is treated by a method described herein.

In some embodiments of the present disclosure, a pharmaceutically acceptable composition may be administered to the skin via spray delivery. In some embodiments, a non-aqueous delivery propellant may be used. Further, in some embodiments, components of the medicaments may be separated at some point prior to application of the medicament. In some embodiments, the photocatalyzable composition may be combined with an aqueous constituent prior to application to the skin sequentially.

Packaging

In some embodiments, the photocatalyzable compositions of the present disclosure may be packed in any suitable packaging for delivering the photocatalyzable compositions for use. Non-limiting examples include bottles or tubes. It will be understood, however, that the package may be structured to prevent the photoactivator from absorbing light, especially light of wavelengths that would activate it. In some embodiments, the package may be opaque. In some embodiments, the package may be comprised of polyethylene terephthalate, high-density polyethylene, low-density polyethylene, or combinations thereof. In some embodiments, the package may be dosed through a cap at the top of the package such that the composition exits the bottle through an opening in the cap. In some embodiments, the opening in the cap may also contain a screen to help facilitate dosing.

In some embodiments, the package may comprise multiple compartments. In some embodiments, the package may comprise two compartments, with a first composition in a first compartment and a second composition in a second compartment. It will be understood that the photoactivator, electron donor, and gasotransmitter salt may be included in either or both of the first and second compartments. In some embodiments, the first composition may comprise the photoactivator and the second composition may comprise the electron donor and gasotransmitter salt.

Gasotransmitter Salt Quenching Test Method

The photoactivators of the present disclosure are evaluated for suitability by the following process.

A suitable wavelength for excitation of the photoactivator is determined by recording a UV/Vis spectrum on any suitable UV/Vis spectrophotometer and identifying an absorption band in the range from about 350 nm to about 750 nm.

The steady state fluorescence is first determined using a fluorescence spectrophotometer to acquire the fluorescence spectrum of the photoactivator. It will be understood by those skilled in the art that the fluorescence produced by the activator varies depending on the fluorescence quantum yield for the structure. The photoactivators are screened through a wide range of concentrations (such as between 1 ppm and 10,000 ppm) to determine the concentration which produces the approximate maximum steady state fluorescence.

Fluorescence quenching is demonstrated by producing solutions of the photoactivator at the concentration determined as described above with a range of concentrations of gasotransmitter salt (such as between 1000 ppm and 100,000 ppm) and electron donor (such as between 1000 ppm and 100,000 ppm).

Photoactivators of the present disclosure in accordance with some embodiments are considered suitable if steady state fluorescence is reduced at least 10% of the initial fluorescence intensity when the photoactivator is dissolved in a 1% solution of gasotransmitter salt and electron donor.

Nitric Oxide Detection Method 10 ppm of 1,2-diaminoanthraquinone is dissolved in the formulation to be tested. The formulation is placed in a UV/Vis cell and exposed to full spectrum (white) light. The light intensity is measured (lux). A UV/Vis spectra is recorded after ten minutes. The reduction in the intensity of the 1,2-diaminoanthraquinone visible absorption peak at 540 indicates that nitric oxide has been formed.

Hydrogen Sulfide Detection Method

The formulation to be tested is placed in a UV/Vis cell and exposed to full spectrum (white) light. The light intensity is measured (lux). Lead acetate paper is contacted with the formulation after ten minutes, a color change to brown/black on the paper indicates the generation of hydrogen sulfide.

Description of Moisturizer Function

Moisturizers or emollients are complex mixtures of chemical agents (often occlusive) to help hold water in the skin after application. Humectants attract moisture and emollients help smooth the skin. Such components are designed to make the external layers of the skin (epidermis) softer and more pliable. Such components also increase the skin's hydration (water content) by reducing evaporation. Occurring skin lipids and sterols, as well as artificial or natural oils, humectants, emollients, and lubricants may be part of the composition of commercial skin moisturizers.

In addition to the aspects and embodiments described and provided elsewhere in the present disclosure, the following non-limiting list of embodiments are also contemplated.

1. A composition comprising:
a water soluble organic photoactivator;
a gasotransmitter salt which converts into a gasotransmitter via electron transfer; and
an electron donor which donates an electron to the photoactivator when the photoactivator is in a photo-excited state.

2. A composition according to clause 1, wherein the photoactivator is selected from benzophenone, anthraquinone, thioxanthone, ketocoumarin, and derivatives thereof.

3. A composition according to clause 2, wherein the photoactivator is water soluble.

4. A composition according to clause 1, wherein the electron donor is selected from alcohols, amines, thiols, sugars, and boranes, and derivatives thereof.

5. A composition according to clause 4, wherein the electron donor is selected from secondary alcohols, tertiary amines, and heteroaromatic thiols, and derivatives thereof.

6. A composition according to clause 5, wherein electron donor is selected from isopropyl alcohol, 2-hexanol, cyclohexanol, triethylamine, ethylene diamine tetracarboxylic acid, diethylene triamine pentacarboxylic acid, and diethylene triamine pentaphosphonic acid.

7. A composition according to clause 1, wherein the gasotransmitter salt is a nitrite or nitrate salt with the formula:

wherein x is 2 or 3; A is selected from the group consisting of monovalent cations, divalent cations, and trivalent cations; wherein m is 1, 2 or 3; in some embodiments, A is selected from the group consisting of Aluminum, Barium, Calcium, Cobalt, Chromium, Copper, Iron, Lithium, Potassium, Rubidium, Magnesium, Manganese, Molybdenum, Nickel, Sodium, Titanium, Vanadium, Zinc, ammonium, alkyl-ammonium, aryl-ammonium, and mixtures thereof in some embodiments, A is selected from the group consisting of lithium, sodium, potassium, magnesium, calcium, ammonium, and mixtures thereof.

8. A composition according to clause 1, wherein the gasotransmitter salt is a sulfate, sulfite, or thiosulfate salt with the formula:

wherein A is selected from the group consisting of monovalent cations, divalent cations, and trivalent cations; in some embodiments, A is selected from the group consisting of Aluminum, Barium, Calcium, Cobalt, Chromium, Copper, Iron, Lithium, Potassium, Rubidium, Magnesium, Manganese, Molybdenum, Nickel, Sodium, Titanium, Vanadium, Zinc, ammonium, alkyl-ammonium, aryl-ammonium, and mixtures thereof; in some embodiments, A is selected from the group consisting of lithium, sodium, potassium, magnesium, calcium, ammonium, and mixtures thereof and a is 1 or 2, b is 3 or 4 and x is 1 or 2 or 3.

9. The composition according to clause 5, wherein the composition is dissolved in water to form an aqueous solution comprising an electron donor which donates an electron to the photoactivator when the photoactivator is in a photo-excited state and/or oxidized state.

10. The composition according to any one of clauses 1-9, wherein the photoactivator can be activated to the photo-excited state by excitation with incident radiation of a wavelength between about 300 nm and about 750 nm; in some embodiments, the wavelength is between about 320 nm and about 420 nm.

11. The composition according to any one of the clauses 1-10, wherein the photo-excited state lifetime is greater than about 50 nanoseconds.

12. The composition according to any one of the clauses 1-11, wherein the photo-excited state of the photoactivator has an energy at least about 100 kJ/mol greater than the ground state of the photoactivator.

13. The composition according to any one of the clauses 1-12, wherein the photoactivator includes a photoactive moiety selected from benzophenone and thioxanthone and derivatives thereof.

14. The composition according to any one of the clauses 1-13, wherein the photoactivator comprises a hydrophilic moiety selected from the group consisting of alcohol, amine, amide, carboxylic acid, sulfonic acid and phosphatealkylene oxide oligomers, alkylene oxide polymers, alkylene oxide copolymers, ethylene glycol, vinyl alcohol, vinyl pyrrolidone, acrylic acid, methacrylic acid, acrylamide, cellulose, carboxymethyl cellulose, chitosan, dextran, 2-ethyl-2-oxazoline, hydroxyethyl methacrylate, vinyl pyridine-N-oxide, diallyl dimethyl ammonium chloride, maleic acid, lysine, isopropyl acrylamide, styrene sulfonic acid, vinyl methyl ether, vinyl phosphonic acid, ethylene imine, and mixtures thereof.

15. The composition according to any one of the clauses 1-14, wherein the gasotransmitter salt is sodium nitrite or sodium sulfite.

16. A method of making a benefit active, the method comprising exposing a composition according to any one of the clauses 1-15 to light.

17. A method of treating acne vulgaris, the method comprising the steps of:
a. contacting the surface of skin affected by acne vulgaris with a composition according to any one of clauses 1-17; and
b. exposing the composition to light.

18. A method of treating a wound, the method comprising the steps of:
a. contacting the surface of wounded tissue with a composition according to any one of clauses 1-17; and
b. exposing the composition to light.

19. A method of treating skin, the method comprising the steps of:
a. contacting a skin surface with a composition according to any one of clauses 1-17; and
b. exposing the composition to light.

20. A method of disinfecting a surface, the method comprising the steps of:
a. contacting the surface with a composition according to any one of clauses 1-17; and
b. exposing the composition to light.

21. A method of removing biofilm from a surface, the method comprising the steps of
a. contacting a biofilm with a composition according to any one of clauses 1-17; and
b. exposing the composition to light.

22. A composition according to clause 1, wherein said composition additionally comprises a hydrophobic base and an amphiphilic compound.

23. A composition according to clause 22, wherein said hydrophobic base comprises a material selected from the group consisting of natural and/or synthetic fats, waxes, and oils.

24. A composition according to clause 1, wherein said composition is in a form selected from the group consisting of ointments, salves, and creams.

25. A composition according to clause 24 additionally comprising a moisture activated active pharmaceutical ingredient.

EXAMPLES

Examples related to the present disclosure are described below. In most cases, alternative techniques can be used. The examples are intended to be illustrative and are not limiting or restrictive of the scope of the invention as set forth in the claims.

Nitric Oxide Photoactivated Wound Formulation

| Ingredient % w/w | A | B | C | D | E |
|---|---|---|---|---|---|
| Purified Water, USP | 85.0 | 85.0 | 85.0 | 85.0 | 85.0 |
| Sodium Nitrite | 1.0 | 3.0 | 0.5 | 5.0 | 3.0 |
| Benzophenone tetracarboxylic acid | 0.01 | 0.1 | | | 0.05 |
| Thioxanthone | | | 0.01 | 0.1 | |
| Glycerol, NF | 10.0 | 10.0 | 10.0 | 10.0 | 10.0 |
| Ethylene diamine tetracarboxylic acid | 1.0 | 0.5 | | | 2 |
| Triethylamine | | | 0.1 | 0.3 | |
| Carbomer | | 1.0 | | 0.3 | 0.5 |

-continued

| Ingredient % w/w | A | B | C | D | E |
|---|---|---|---|---|---|
| Homopolymer Type A, NF Carbopol 974P | | | | | |
| Carbomer Interpolymer Type B, NF Carbopol ETD2020NF | — | 0.5 | | 1.0 | |
| Trolamine, NF | To pH 7 | — | | To pH 7 | |
| 0.1M Phosphate Buffer | — | To pH 7 | To pH 7 | — | To pH 7 |
| Purified water USP | To 100 | To 100 | To 100 | To 100 | To 100 |

To test the above formulations, 10 ppm of 1,2-diaminoanthraquinone is dissolved in the formulations. The formulations are placed in a UV/Vis cell and exposed to full spectrum (white) light. The light intensity is measured (lux). A UV/Vis spectra is recorded after ten minutes. The reduction in the intensity of the 1,2-diaminoanthraquinone visible absorption peak at 540 indicates that nitric oxide has been formed.

Hydrogen Sulfide Photoactivated Wound Formulation

| Ingredient % w/w | A | B | C | D |
|---|---|---|---|---|
| Purified Water, USP | 85.0 | 85.0 | 85.0 | 85.0 |
| Sodium Sulfite | 1.0 | 3.0 | 0.5 | 5.0 |
| Benzophenone tetracarboxylic acid | 0.01 | 0.1 | 0.001 | 0.5 |
| Glycerol, NF | 10.0 | 10.0 | 10.0 | 10.0 |
| Ethylene diamine tetracarboxylic acid | 1 | 0.5 | | |
| Diethylene triamine pentacarboxylic acid | | | 0.1 | 0.3 |
| Carbomer Homopolymer Type A, NF Carbopol 974P | 1.0 | 0.3 | — | |
| Carbomer Interpolymer Type B, NF Carbopol ETD2020NF | — | — | 0.5 | 1.0 |
| Trolamine, NF | To pH 7 | — | | To pH 7 |
| 0.1M Phosphate Buffer | — | To pH 7 | To pH 7 | — |
| Purified water USP | To 100 | To 100 | To 100 | To 100 |

To test the above formulations, the formulations are placed in a UV/Vis cell and exposed to full spectrum (white) light. The light intensity is measured (lux). Lead acetate paper is contacted with the formulation after ten minutes to determine the generation of hydrogen sulfide.

Nitric Oxide Photoactivated Skin Care Formulation

| Ingredient % w/w | A | B | C | D | E |
|---|---|---|---|---|---|
| Purified Water, USP | 60.0 | 60.0 | 60.0 | 60.0 | 60.0 |
| Sodium Nitrite | 1.0 | 3.0 | 0.5 | 5.0 | 3.0 |
| Benzophenone tetracarboxylic acid | 0.01 | 0.1 | | | 0.05 |
| Thioxanthone | | | 0.01 | 0.1 | |
| Ethylene diamine tetracarboxylic acid | 1 | 2 | | | 0.5 |
| Diethylenetriaimne pentacarboxylic acid | | | 1 | 0.5 | |
| Beeswax | 3 | 5 | 4 | 5 | 3 |
| Lanolin | 3 | 2 | 3 | 1 | 2 |
| Lecithin | 10 | 15 | | | |
| Coconut oil | | | 12 | 10 | 15 |
| Glyceryl stearate | 5 | 7 | 10 | 5 | 7 |
| Hydroxyethyl cellulose | | 3 | 3 | 2 | 2 |
| Carbomer Homopolymer Type A, NF Carbopol 974P | 1.0 | | | | |
| Trolamine, NF | To pH 7 | — | | To pH 7 | |
| 0.1M Phosphate Buffer | — | To pH 7 | To pH 7 | — | To pH 7 |
| Purified water USP | To 100 | To 100 | To 100 | To 100 | To 100 |

To test the above formulations, 10 ppm of 1,2-diaminoanthraquinone is dissolved in the formulations. The formulations are placed in a UV/Vis cell and exposed to full spectrum (white) light. The light intensity is measured (lux). A UV/Vis spectra is recorded after ten minutes. The reduction in the intensity of the 1,2-diaminoanthraquinone visible absorption peak at 540 indicates that nitric oxide has been formed.

Hydrogen Sulfide Photoactivated Skin Formulation

| Ingredient % w/w | A | B | C | D | E |
|---|---|---|---|---|---|
| Purified Water, USP | 60.0 | 60.0 | 60.0 | 60.0 | 60.0 |
| Sodium sulfite | 1.0 | 3.0 | 0.5 | 5.0 | 3.0 |
| Benzophenone tetracarboxylic acid | 0.01 | 0.1 | | | 0.05 |
| Thioxanthone | | | 0.01 | 0.1 | |
| Ethylene diamine tetracarboxylic acid | 1 | 2 | | | 0.5 |
| Diethylenetriaimne pentacarboxylic acid | | | 1 | 0.5 | |
| Beeswax | 3 | 5 | 4 | 5 | 3 |
| Lanolin | 3 | 2 | 3 | 1 | 2 |
| Lecithin | 10 | 15 | | | |
| Coconut oil | | | 12 | 10 | 15 |
| Glyceryl stearate | 5 | 7 | 10 | 5 | 7 |
| Hydroxyethyl cellulose | | | 3 | 2 | 2 |
| Carbomer Homopolymer Type A, NF Carbopol 974P | 1.0 | | | | |
| Trolamine, NF | To pH 7 | — | | To pH 7 | |
| 0.1M Phosphate Buffer | — | To pH 7 | pH 7 | — | To pH 7 |
| Purified water USP | To 100 | To 100 | To 100 | To 100 | To 100 |

To test the above formulations, the formulations are placed in a UV/Vis cell and exposed to full spectrum (white) light. The light intensity is measured (lux). Lead acetate paper is contacted with the formulation after ten minutes to determine the generation of hydrogen sulfide.

While embodiments have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A composition comprising:
    an organic photoactivator to receive an electron when the photoactivator is in a photo-excited state;
    an electron donor which donates the electron to the photoactivator when the photoactivator is in the photo-excited state to reduce the photoactivator and initiate conversion of a gasotransmitter salt into a gasotransmitter; and
    the gasotransmitter salt which converts into the gasotransmitter via reduction when the photoactivator is reduced by the electron, wherein the electron donor is selected from alcohols, amines, thiols, sugars, and boranes, and derivatives thereof, wherein the gasotransmitter salt is a nitrite or nitrate salt with the formula:

$A[NO_x]_m$ wherein x is 2 or 3;

wherein A is selected from monovalent cations, divalent cations, and trivalent cations;

wherein m is 1, 2 or 3; and wherein the composition is in a form selected from the group consisting of ointments, salves, and creams.

2. The composition of claim 1, wherein the electron donor is selected from secondary alcohols, tertiary amines, and heteroaromatic thiols, and derivatives thereof.

3. The composition of claim 2, wherein the electron donor is selected from isopropyl alcohol, 2-hexanol, cyclohexanol, triethylamine, ethylene diamine tetracarboxylic acid, diethylene triamine pentacarboxylic acid, and diethylene triamine pentaphosphonic acid.

4. The composition of claim 2, wherein the composition is dissolved in water to form an aqueous solution comprising an electron donor which donates an electron to the photoactivator when the photoactivator is in a photo-excited state and/or oxidized state.

5. The composition of claim 1, wherein the photoactivator is activated to the photo-excited state by excitation with incident radiation of a wavelength between about 300 nm and about 750 nm.

6. The composition of claim 1, wherein the photo-excited state lifetime is greater than about 50 nanoseconds.

7. The composition of claim 1, wherein the photo-excited state of the photoactivator has an energy greater than about 100 kJ/mol more than a ground state of the photoactivator.

8. The composition of claim 1, wherein the photoactivator includes a photoactive moiety selected from benzophenone and thioxanthone and derivatives thereof.

9. The composition of claim 1, wherein the photoactivator comprises a hydrophilic moiety selected from the group consisting of alcohol, amine, amide, carboxylic acid, sulfonic acid and phosphate alkylene oxide oligomers; alkylene oxide polymers; alkylene oxide copolymers; ethylene glycol; vinyl alcohol; vinyl pyrrolidone; acrylic acid; methacrylic acid; acrylamide; cellulose; carboxymethyl cellulose; chitosan; dextran; 2-ethyl-2-oxazoline; hydroxyethyl methacrylate; vinyl pyridine-N-oxide; diallyl dimethyl ammonium chloride; maleic acid; lysine; isopropyl acrylamide; styrene sulfonic acid; vinyl methyl ether; vinyl phosphonic acid; and ethylene imine; and mixtures thereof.

10. The composition of claim 1, wherein the gasotransmitter salt is sodium nitrite.

11. A method of making a benefit active, the method comprising exposing the composition of claim 1 to light.

12. A method of treating acne vulgaris, the method comprising:
contacting the surface of skin affected by acne vulgaris with the composition according to claim 1; and
exposing the composition to light.

13. A method of treating a wound, the method comprising:
contacting the surface of wounded tissue with the composition according to claim 1; and
exposing the composition to light.

14. A method of treating skin, the method comprising:
contacting a skin surface with the composition according to claim 1; and
exposing the composition to light.

15. A method of disinfecting a surface, the method comprising:
contacting the surface with the composition according to claim 1; and
exposing the composition to light.

16. A method of removing biofilm from a surface, the method comprising:
contacting a biofilm with the composition according to claim 1; and
exposing the composition to light.

17. The composition of claim 1, wherein the composition further comprises a hydrophobic base and an amphiphilic compound.

18. The composition of claim 17, wherein said hydrophobic base comprises a material selected from the group consisting of natural fats, synthetic fats, waxes, and oils.

19. The composition of claim 1, further comprising a moisture activated active pharmaceutical ingredient.

20. The composition of claim 5, wherein the photoactivator is activated to the photo-excited state by excitation with incident radiation of a wavelength between about 320 nm and about 420 nm.

* * * * *